United States Patent [19]

Gruszecki et al.

[11] 4,439,363

[45] Mar. 27, 1984

[54] ACETYLMETHYL ESTER OF HETACYLLIN AND/OR SALTS OF THIS ESTER

[75] Inventors: Wojciech A. Gruszecki, Gdansk; Irena M. Busko-Oszczopowicz, Warsaw; Maria Gdulewicz-Gruszecka, Gdansk; Jerzy J. Cieslak, Warsaw; Edward Borowski, Gdansk; Teresa Gumiezna, Warsaw, all of Poland

[73] Assignees: Politechnika Gdanska, Gdansk; Instytut Przemyslu Farmaceutyoznego Majakowskiego, Warsaw, both of Poland

[21] Appl. No.: 352,118

[22] Filed: Feb. 25, 1982

Related U.S. Application Data

[63] Continuation of Ser. No. 158,399, Jun. 11, 1980, abandoned.

[30] Foreign Application Priority Data

Jun. 20, 1979 [PL] Poland .................................. 216450

[51] Int. Cl.³ .................... C07D 499/46; A61K 31/43
[52] U.S. Cl. .......................... 260/239.1; 260/245.2 R; 424/271; 424/270
[58] Field of Search ..................... 260/245.2 R, 239.1; 424/270, 271

[56] References Cited

U.S. PATENT DOCUMENTS 3,996,236 12/1976 Sleezer et al. .................... 260/245.2

*Primary Examiner*—Nicholas S. Rizzo

[57] ABSTRACT

The acetylmethyl ester of hetacyllin and/or its salts of an organic or inorganic acid are described and methods for their synthesis wherein a tertiary amine and chloroacetone are introduced to hetacyllin in an organic solvent or chloroacetone is introduced to hetacyllin in the form of a salt with an alkali metal in an organic solvent, and then from the reaction mixture, the acetylmethyl ester of hetacyllin is isolated in free form and, if desired, a salt of the ester is obtained by reaction with an organic or inorganic acid in an organic solvent.

As tertiary amines, trialkylamine, N-methylpiperidine, N-ethylpiperidine or N-methylmorpholine are used; as organic solvents in obtaining the ester, dimethylformamide, dimethylacetamide or dimethylsulfoxide are used. In obtaining salts of the ester the organic solvents used are aliphatic alcohols of a chain length $C_2$–$C_5$; ketones, preferably acetone; ethers, such as diethyl, dipropyl, diisopropyl, dibutyl ethers, or their mixtures.

The obtained compounds show an antibacterial action like ampicillin but after administration per os they show a considerably higher level of the antibiotic than that after administration of free ampicillin or its esters.

2 Claims, 1 Drawing Figure

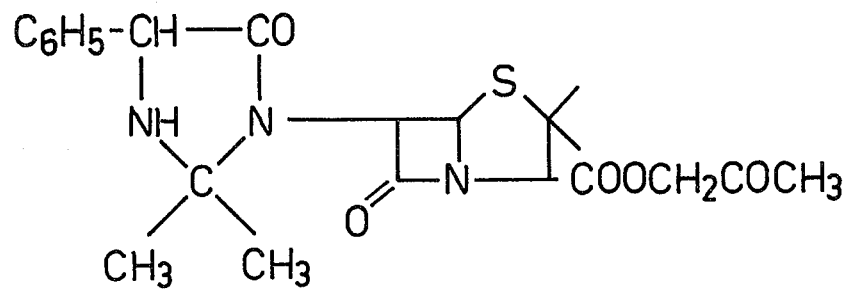
Wzór 1
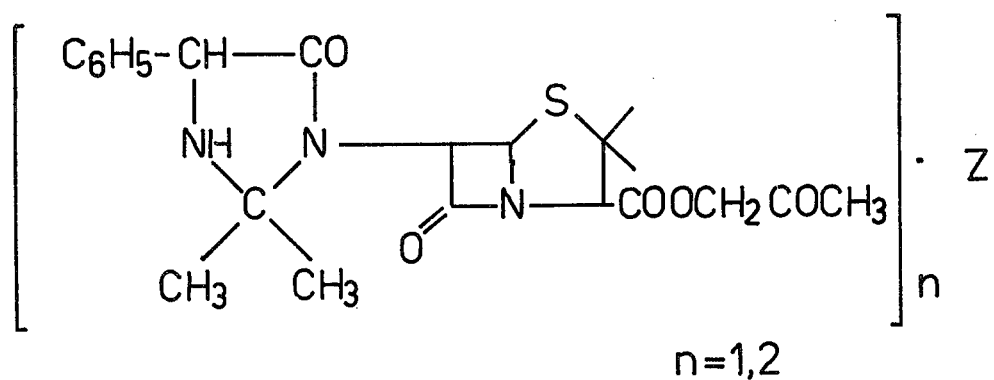
n=1,2
Wzór 2
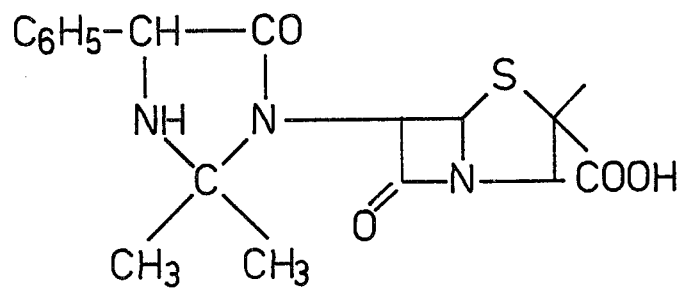
Wzór 3

| Compound | 5' | 10' | 15' | 30' | 45' | 1 hr | 2 hrs | 3 hrs | 4 hrs | 5 hrs | 6 hrs |
|---|---|---|---|---|---|---|---|---|---|---|---|
| /formula 2/, Z = HCl | | | | | | | | | | | |

As shown from table 1, hetacyllin in relation to ampicillin after administration per os gives lower levels of ampicillin in plasma during the first hour after administration, and slightly higher levels during subsequent hours, i.e. 2–6. On the other hand, the novel ester of hetacyllin of the formula 1 obtained by the method according to the invention after introduction per os, gives very high levels of ampicillin in plasma. During the first hour after administration of the ester the maximum level is more than two times higher than the analogous level obtained after administration of ampicillin and more than four times higher than the maximum level after administration of hetacyllin.

The highest level of ampicillin in plasma is obtained after an introduction per os of the hydrochloride of acetylmethyl ester of hetacyllin. It is over four times higher than the analogous level obtained after administration of ampicillin and over seven times higher than after administration of hetacyllin.

The hydrochloride of the ester gives also nearly two times higher level of ampicillin in plasma than the level obtained after administration of the free ester.

After administration of said hydrochloride of the ester very high levels of ampicillin are also obtained in particular organs of rats. The levels in lungs, kidneys and liver are correspondingly ten times, four times, and one and a half times higher than after administration per os of equivalent doses of ampicillin.

Compounds obtained by the method according to the invention, especially hydrochloride of the ester, after an introduction per os show also higher levels in plasma than esters of ampicillin presently known and applied in therapeutics, such as pivaloyloxymethyl ester (pivampicillin), 1-ethoxycarbonyloxyethyl ester (bacampicillin), or phtalidyl ester (talampicillin, talpen).

In these esters the active form of the antibiotic is also free ampicillin [Structure Activity Relationships among the semisynthetic antibiotic. Perlman Edited by Academic Press 1977, p. 74].

For example, after adminstration per os of the hydrochloride of the ester of hetacyllin the level of the antibiotic obtained in the plasma of rats is two times higher, and in kidneys - one and a half times higher than after the introduction of equivalent does of pivampicillin by the same route.

Further compounds of formulae 1 and 2 do not show an increased toxicity in relation to the initial ampicillin. For example, the acute toxicity of acetylmethyl ester of hetacyllin and its hydrochloride after administration per os, in white mice of the Swiss tribe is very low, the $LD_{50}$ being greater than 5 g/kg of body weight. Such low toxicity of compounds obtained by the method according to the invention is probably related to the formation of hydroxyacetone in plasma under the effect of an enzymatic hydrolysis of the ester. Hydroxyacetone is characterized by minimal toxicity, and therefore does not cause an increase of toxicity of the compounds according to the invention.

On the other hand, the previously mentioned esters of ampicillin known and used in therapeutics, as a result of their enzymatic hydrolysis in plasma, release much more toxic substances which increase the toxicity of these compounds in relation to the initial ampicillin.

Moreover, the hydrochloride salt of the ester of formula 2, does not show any action upon the central nervous system in mice nor upon blood arterial pressure and heat function in rats.

An advantage of the present invention is the simplicity of chemical operations with good yields of the compounds of formulae 1 and 2, which renders it possible to use the said methods in industrial production.

The compounds according to the invention when introduced per os to humans and animals provide high concentrations of the antibiotic in plasma, tissues and body fluids. Very low toxicity of these compounds makes it possible to administer them in therapeutics an antibacterial agents.

Said compounds and the method of obtaining them are illustrated by the examples.

EXAMPLE 1.

Into 14 g/0.036 mole/ of hetacyllin in 25 ml of dry dimethylformamide, 6.0 ml /0.043 mole/ of triethylamine was added at a temperature of 0° C. and the mixture thus obtained was stirred for 10 minutes, and then 6.2 ml /0.072 mole/ of chloroacetone was added dropwise and the mixture was then stirred at a temperature of 0–5° C. during 48 hours. After cooling to a temperature of −15° C., at intense stirring, 50 ml of water was added at first, and then after 0.5 hour further 200 ml of water was added, and thus slow crystallization of ester was obtained. After one hour the mixture was filtered, the obtained white crystalline precipitate was then washed three times with 20 ml of cold water and airdried. 11.7 g of ester was obtained which is 70% of the theoretical yield.

Purity according to iodmtric determinations: 93.1%. Melting temperature: 86°–88° C. Infrared spectrum shows, within the range of 1600–1800 cm$^{-1}$, the following characteristic bands: 1685 cm$^{-1}$ (C=O amide); 1715, 1755 cm$^{-1}$(C=O ester); 1780 cm$^{-1}$ (C=O β-lactam).

In the NMR spectrum recorded in DMSO at 60 MHz the following bands are observed (δppm): 1.31 s (3H); 1.49 s (3H); two CH$_3$ groups in a side chain; 1.49 s (3H); 1.60 s (3H); two groups CH$_3$ at C—2; 2.08 s (3H); CH$_3$ from CH$_3$COCH$_2$—; 4.42 s (H) C-3; 4,82 s (2H) CH$_2$ from CH$_3$COCH$_2$—;

5.02 d /H/  
5.38 d /H/ } C-5; C-6 J = 4.5

7.1–7.5 m (5H) C$_6$H$_5$—.

EXAMPLE 2.

To 14.8 g (0.036 mole) of a sodium salt of hetacyllin in 70 ml of dry dimethylsulfoxide 6.2 ml (0.072 mole) of chloroacetone was added at a temperature of 0° C., and

ACETYLMETHYL ESTER OF HETACYLLIN AND/OR SALTS OF THIS ESTER

This is a continuation, of application Ser. No. 158,399, filed June 11, 1980, now abandoned.

The subject of the invention is a new ester of hetacyllin according to the formula 1

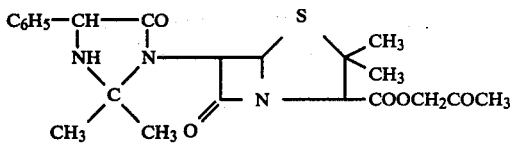

and/or its salts of the formula 2

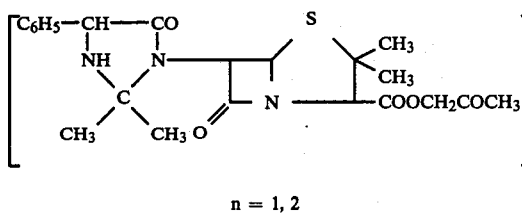

n = 1, 2 wherein Z is a molecule of a pharmaceutically acceptable organic or an inorganic acid, whereas n=1 or 2, as well as the method for preparing same. These compounds have not yet been described in the literature.

Acethylemthyl ester of hetacyllin of the formula 1 and/or its salts of the formula 2 wherein Z denotes an organic or an inorganic acid, and n=1 or 2, and the method of obtaining them are the subject of this invention. The method of obtaining of acetylmethyl ester of hetacyllin of the formula 1 or its salts of the general formula 2 of an organic or an inorganic acid, whereas n=1-2, according to the invention comprises the steps wherein to a solution of hetacyllin of the formula 3

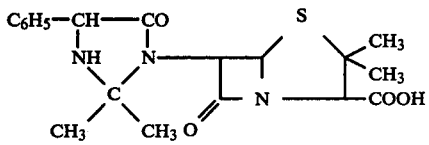

in an organic solvent a tertiary amine and chloroacetone are introduced and the ester thus obtained is isolated from the reaction mixture in its free form and, if desired, is converted into the salt with an organic or an inorganic acid in an organic solvent.

As the solvent the synthesis of the ester of hetacyllin, dimethylformamide, dimethylacetamide or dimethylsulfoxide is used.

As tertiary amines trialkylamine, N-methylpiperidine, N-ethylpiperidine or N-methylmorpholine are used.

The obtained ester is converted into the salt in a medium of aliphatic alcohols of the chain length of C2 to C5 or ethers such as diethyl, dipropyl, diisopropyl, dibutyl ether or ketones, preferably acetone, or their mixtures.

Another method of obtaining the acetyl methyl ester of hetacyllin of the formula 1 and/or its salts of formula 2 according to this invention comprises the steps wherein hetacyllin in the form of a salt with an alkali metal in an organic solvent is reacted with chloroacetone, and the ester thus obtained is separated from the reaction mixture by the known methods and in a free form and, if necessary, it is converted into its salt with an organic or an inorganic acid in a medium of an organic solvent. The solvent used in obtaining of the ester of hetacyllin is dimethylformamide, dimethylacetamide or dimethylsulfoxide.

The obtained ester is converted into its salt in a medium of aliphatic alcohols of the chain length of C2–C5 or ethers such as diethyl, dipropyl, diisopropyl, dibutyl ether, or ketones, preferably acetone, or their mixtures.

The investigation has been based on the method of mass spectrometry and it permits to presume that the discussed compounds and their therepeutic salts may appear in polymeric forms.

New compounds of formulae 1 and 2 exhibit in vivo and in vitro, a strong antibiotic action against Gram-positive and Gram-negative pathogenic strains. Similar to ampicillin and its derivatives as used in therapeutics, causing after administration of relatively small doses an achievement of very high levels of the active form of the antibiotic in blood, tissues and body fluids.

Hetacyllin of the formula 3 which is the starting material is a derivative of ampicillin. It is obtained as a result of the reaction of ampicillin with acetone. This compound hydrolyzes in the blood and in body fluids giving ampicillin and acetone.

As the active form of the new compounds of the formulae 1 and 2 free ampicillin is produced in the blood and in body fluids as a result of an enzymatic hydrolysis of the ester part of hetacyllin and acetone group attached to the amine group.

In table 1 are presented levels at timed intervals of the antibiotic in $\mu$g/ml in plasma of rats after administration of identical doses as calculated in terms of free ampicillin of the said compounds, i.e. hetacyllin (formula 3), acetylmethyl ester of hetacyllin (formula 1), hydrochloride of acetylmethyl ester of hetacyllin (formula 3) and free ampicillin.

TABLE 1

| | time | | | | | | | | | | |
|---|---|---|---|---|---|---|---|---|---|---|---|
| Compound | 5' | 10' | 15' | 30' | 45' | 1 hr | 2 hrs | 3 hrs | 4 hrs | 5 hrs | 6 hrs |
| Ampicillin | 3.74 | 3.86 | 7.42 | 16.49 | 14.00 | 12.14 | 2.47 | 1.03 | 0.46 | 0.46 | 0.31 |
| Hetacyllin /formula 3/ | 2.32 | 3.24 | 4.06 | 7.00 | 9.10 | 9.17 | 7.70 | 3.16 | 0.98 | 1.30 | 0.93 |
| Acetylmethyl ester of hetacyllin /formula 1/ | 29.0 | 37.5 | 39.2 | 24.3 | 15.9 | 8.6 | 0.48 | 0.34 | 0.04 | — | — |
| Hydrochloride of acetylmethyl ester of hetacyllin | 38.8 | 64.5 | 66.0 | 52.0 | — | 28.5 | 5.01 | 4.2 | 1.24 | 0.17 | 0.1 | the mixture was stirred at a temperature of 0°-5° C. during 48 hours. Then the solution was poured, at intense stirring, into 1.5 l of 10% solution of sodium chloride in water and after 0.5 hour of stirring the precipitate obtained was filtered off, washed three times with 20 ml of cold water and air-dried. 8.7 g of ester was obtained which is 54% of the theoretical yield. Melting temperature: 84°-86° C. Purity according to iodometric determinations: 92.3%.

EXAMPLE 3

2.5 g (0.0056 mole) of acetylemthyl ester of hetacyllin was dissolved in 26 ml of a solution consisting of isopropyl alcohol and acetone (1:1 by weight) and after cooling down to the temperature of +7° C. 1.4 ml of 4n HCl (0.0056 mole) in isopropyl alcohol was added. After several minutes of stirring crystallization of hydrochloride started. The obtained precipitate was filtered off and washed 3 times with 5 ml of a solution consisting of isopropoyl alcohol and acetone (1:1 by weight), and then with 10 ml of diethyl ether, and air-dried. 2.35 g of hydrochloride was obtained which is 85% of the theoretical yield.

Purity according to iodometric determinations: 91.1% Infrared spectrum within the range of 1600–1800 cm$^{-1}$ shows the following characteristic bands: 1710 cm$^{-1}$ (C=O amide); 1720, 1750 cm$^{-1}$ (C=O ester); 1775 cm$^{-1}$ (C=O β-lactam). In the NMR spectrum recorded in DMSO at 60 MHz the following bands are observed:

1.54 s (3H); 1.61 s (3H) two CH$_3$ groups at C-2; 1.70 s (3H); 1.76 s (3H) two CH$_3$ groups in a side chain; 2.08 d (3H); CH$_3$ from CH$_3$COCH$_2$—; 4.45 s (H); C-3; 5.25–5.6 m (2H); C-5, C-6; 7.35–7.55 m (5H); C$_6$H$_5$—.

EXAMPLE 4

2.5 g (0.0056 mole) of acetylmethyl ester of hetacyllin was added to 26 ml of a solution consisting of isopropyl alcohol and acetone (1:1 by weight) and after cooling to a temperature of +7° C., 1.4 ml of 4 n solution of HCl in isopropyl alcohol was added. After several minutes of stirring crystallization of hydrochloride started. Then 10 ml of dibutyl ether was added and after 15 minutes of stirring the obtained precipitate was filtered off and washed 3 times with 5 ml of a solution consisting of isopropyl alcohol and acetone (1:1), and then 10 ml of dimethyl ether was added, and air-dried.

2.3 g of the hydrochloride of acetylmethyls ester of hetacyllin was obtained which is 83% of the theoretical yield. Purity according to iodometric determinations: 95.7%.

EXAMPLE 5

Procedure was the same as in above example 4 but instead of the hydrochloride solution a solution of sulphuric acid was used and the sulfate of acetylmethyl ester of hetacyllin was obtained with 89% of the theoretical yield. Purity according to iodometric determinations: 93.8%.

Infrared spectrum shows within the range of 1600–1800 cm$^{-1}$ the following characteristic bands: 1710 cm$^{-1}$ (C=O), 1715, 1750 cm$^{-1}$ (C=O ester), 1780 cm$^{-1}$ (C=O β-lactam). In the NMR spectrum recorded in DMSO at 60 MHz the following bands are observed:

1.55 s (3H); 1.60 s (3H) two CH$_3$ groups at C-2; 1.68 s (3H); 1.76 s (3H) two CH$_3$ groups in a side chain; 2.1 s (3H); CH$_3$ from CH$_3$COCH$_2$—; 4.5 s (H); C-3; 4.9 s (2H); CH$_2$ from CH$_3$COCH$_2$—; 5.15–5.55 m (2H); C-5, C-6; 7.30–7.55 m (5H); C$_6$H$_5$—.

EXAMPLE 6

Procedure was the same as in Example 4 but instead of a solution of HCl a solution of acetic acid was used and the acetate of acetylemthyl ester of hetacyllin was obtained with 72% of the theoretical yield.

Purity according to iodometric determinations: 93.8%.

What is claimed is:

1. An acetylmethyl ester of hetacyllin of the formula:

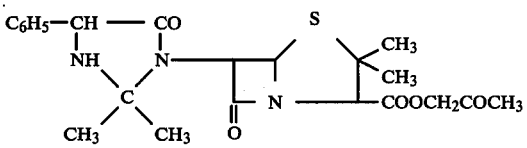

and the non-toxic, pharmaceutically acceptable salts thereof.

2. The hydrochloride salt of the ester according to claim 1.

* * * * *